United States Patent [19]

Adler-Moore et al.

[11] Patent Number: 5,656,287
[45] Date of Patent: Aug. 12, 1997

[54] LIPOSOMAL CYCLOSPORIN FORMULATIONS AS AGENTS FOR IMMUNOSUPPRESSION AND MULTIPLE DRUG RESISTANT INDICATIONS

[75] Inventors: Jill Adler-Moore, Altadena; Su-Ming Chiang, Canoga Park, both of Calif.

[73] Assignee: NeXstar Pharmaceuticals, Inc., Boulder, Colo.

[21] Appl. No.: 472,635

[22] Filed: Jun. 7, 1995

[51] Int. Cl.$^6$ ........................................ A61K 9/127
[52] U.S. Cl. ............................................. 424/450
[58] Field of Search .................... 424/450; 428/402.02

[56] References Cited

U.S. PATENT DOCUMENTS

| | | | |
|---|---|---|---|
| 4,608,211 | 8/1986 | Handjani | 264/4.6 |
| 4,663,167 | 5/1987 | Berostein | 514/37 |
| 4,797,285 | 1/1989 | Barenholz et al. | 424/450 |
| 4,952,405 | 8/1990 | Young | 424/423 |
| 4,963,362 | 10/1990 | Rahman | 424/450 |
| 5,000,887 | 3/1991 | Tenzel et al. | 264/4.6 |
| 5,023,087 | 6/1991 | Yau-Young | 424/450 |

FOREIGN PATENT DOCUMENTS

| | | |
|---|---|---|
| WO90/00389 | 1/1990 | WIPO. |
| WO91/04019 | 4/1991 | WIPO. |

OTHER PUBLICATIONS

Szoka Ann. Rev. Biophys. Bioey. 1980, 9, p. 467.
Hsieh et al. "Preliminary Report: The Use of Liposome-Encapsulated Cyclosporin In a Rat Model Transplantation Proceedings", vol. XVII, pp. 1397–1400. (Feb., 1985).
Stuhne-Sekalec et al. "Encapsulation of Cyclosporine by Phosphatidylinositol-Cholesterol Liposomes", Transplantation vol. 41, pp.659–660 (1986).
Stuhne-Sekalec et al. "Co-encapsulation of Cyclosporin and Insulin by Liposomes", J. Biochem. Biophys, Methods vol.13, pp.23–27(1986).
Gruber et al., "liposomal Formulation Eliminates Acute Toxicity and Pump Incompatibility of Parenteral Cyclosporin", Pharm. Res. vol. 5, pp. 601–607 (1989).
Stuhne-Sekalec et al., "Liposomes as Cyclosporin A Carriers: Positively Charged . . . Phosphatidylinositol", J. Microencapsulation vol. 6, pp.177–182 (1989).
Venkataram et a. "Pharmacokinetics of Two Alternative Dosage Forms for Cyclosporine: Liposomes and Intralipid" J. Pharm. Sci. vol. 79, pp.216–219 (1990).
Stuhne-Sekalec et al. "Liposomes as Cyclosporin A Carriers: The Influence . . . Cyclosporin A", J Microencapsulation vol. 8, p.283–294 (1991).
Stuhne-Sekalec et al. "Liposomes as Carriers of Cyclosporin A, J. Microencapsulation vol. 8", pp.441–446 (1991).
Stuhne-Sekalec et al. "Liposomes as Cyclosporin A Carriers: ESR Study . . . Phosphatidylglycerol Liposomes", J. Microencapsulation vol. 8, pp.455–463 (1991).
Deamer: Liposome Prep. Chap. I, p. 27 (1983).
Szoke: Ann. Rev. Biophys. Bioeng. vol. 9, p.467 (1980).

Van de Vrie, W., "In vitro and in vivo chemosensitizing effect of cycloproin A on an intrinsic multidrug–resistant rat colon tumour", Cancer Research Clinical Oncology vol. 119, pp.609–614 (1993).
Freise, Chris E., "The increased efficacy and decreased nephrotoxicity of a cyclosporine liposome Transplantation vol. 57", No. 6, pp.928–932 (Mar. 1994).
Sonneveld, P, "Clinical modulation of multidrug resistance in mulitple myeloma: Effect of cyclosporin on resistant tumor cells", Journal of Clinical Oncology vol. 12, No. 8, pp.1584–1591 (Aug. 1994).
Colombo, Tina, "Cyclosporin a markedly changes the distribution of doxorubicin in mice and rats The Journal of Pharmacology and Experimental Therapeutics", vol. 269, No.1, p.22–27 (1994).
Yano, Seiji, "Cyclosporin a enhances susceptibility of multi–drug resistant human cancer cells to anti–P–glycoprotein antibody–dependent cytotxicity of monocytes, but not of lymphocytes", J. Cancer Res. vol. 85, p.194–203 (Feb. 1994).
van der Graaf, Winette T.A., "Effects of amiodarone, cyclosporin A, and PSC 833 on the cytotoxicity of mitoxantrone, doxorubicin and vincristine in non–P–glycoprotein human small cell lung cancer cell lines", Cancer Research vol. 54, pp.5368–5373 (Oct. 15, 1994).
Erlichman, Charles, "Phase I pharmacokinetic study of cyclosporin a combined with doxorubicin Cancer Research vol. 53", p.4837–4842 (Oct. 15, 1993).
Sonneveld, Pieter, "Modulation of multidrug-resistant multiple myeloma by cyclosporin", The Lancet vol. 340, No. 8814, pp.255–259 (Aug. 1, 1992).
Samuels, Brian L., "Modulation of vinblastine resistance with cyclosporine: A phase I study", Clinical Pharmacology & Therapeutics vol. 54, No. 4, pp.421–429 (Oct. 1993).
Sikic, Branimir I., "Modulation of multidrug-resistance: At the Threshold", Journal of Clinical Oncology vol. 11, No. 9, pp.1629–1635 (Sep. 1993).
Thierry, Alain R., "Effect of liposomes on P–glycoprotein function in multidrug–resistant cells", Biochemical and Biophysical Research Communications vol. 187, No. 2, pp.1098–1105 (Sep. 16, 1992).
Rahman, Aquilur, "Liposome–mediated modulation of multidrug resistance in human HL–60 leukemia cells", Journal of the National Cancer Institute vol. 84, No. 24, pp.1909–1915 (Dec. 16, 1992).
Dalton, William S., "Drug resistance modulation in the laboratory and the clinic", Seminars in Oncology vol. 20, No. 1, pp. 64–69 (Feb. 1993).

(List continued on next page.)

*Primary Examiner*—Gollamudi S. Kishore
*Attorney, Agent, or Firm*—NeXstar Pharmaceuticals, Inc.

[57] ABSTRACT

An improved liposomal cyclosporin therapeutic formulation, comprising phosphatidylcholine, cholesterol, dimyristoylphosphatidylglycerol and a cyclosporin in a mole ratios of about 21:0.5:3:1 to 21:1.5:3:1 and 24:0.5:3:1 to about 24:1.5:3:1. The formulations are useful as immunosuppressive agents and enhancers of antineoplastic agents in drug resistant cancer cells.

7 Claims, No Drawings

OTHER PUBLICATIONS

Clynes, Martin, "Cellular models for multiple drug resistance in cancer", In Vitro Cell. Dev. Biol. 29A, pp. 171–179 (Mar. 1993).

Dietel, Manfred, "Second international symposium on cytostatic drug resistance", Cancer Resear vol. 53, pp. 2683–2688 (Jun. 1, 1993).

Twentyman, Peter R., "A possible role for cyclosporins in cancer chemotherapy", Anticancer Research vol. 8, pp.985–994 (1988).

List, Alan F., "Phase I/II trial of cyclosporine as a chemotherapy resistance modifier in acute leukemia", Journal of Clinical Oncology vol. 11, No. 9, pp. 1652–1660 (Sep. 1993).

Boesch, Danielle, "In vivo circumvention of P-glycoprotein–mediated multidrug resistance of tum cells with SDZ PSC 833", Cancer Research vol. 51, pp. 4226–4233 (Aug. 15, 1991).

Yahanda, Anne M., "Phase I trial of etoposide with cyclosporine as a modulator of multidrug resistance", Journal of Clinical Oncology vol. 10, No. 10, pp.1624–1634 (Oct. 1992).

Benedicte Jachez, Rene, "Restoration of taxol sensitivity of multidrug resistant cells by the cyclosporine SDZ PSC 833 and the cyclopeptolide SDZ 280–446", Journal of the National cancer Institute vol. 85, No. 6, pp.478–483 (Mar. 17, 1993).

Slater, Lewis M., "Cyclosporin a reverses vincristine and daunorubicin resistance in acute lymphatic leukemia in vitro", Cyclosporin A Corrects Vincristine and Daunorubicin Resistance vol. 77, pp.1405–1408 (Apr. 1986).

Friche, Ellen, "Comparison of cyclosporin A and SDZ PSC 833 as multidrug resistance modulators in a daunorubicin resistant Ehrlich ascites tumor", Cancer Chemotherapy and Pharmacology vol. 30, pp.235–237 (1992).

Shoji, Y, "Verapamil and cyclosporin A modulate doxorubicin toxicity by distinct mechanisms", Cancer Letters vol. 57,pp.209–218 (1991).

Hu, Xiu F., "Combined use of cyclosporin A and verapamil in modulating multidrug resistance in human leukemia cell lines", Cancer Research vol. 50, pp.2953–2957 (May 15, 1990).

Meador, Josephine, "Enhancement by cyclosporin A of daunorubicin efficacy in Ehrilich ascites carcinoma and murine hepatoma 129", Cancer Research vol. 47, pp.6216–6219 (Dec. 1, 1987).

Kuhl, Jorn–Sven, "Use of etoposide in combination with cyclosporine for purging multidrug resistant leukemic cells from bone marrow in a mouse model", Advances in Bone Marrow Purging and Processing, pp.25–34 (1992).

Nygren, P. "Verapamil and cyclosporin a sensitize human kidney tumor cells to vincristine in absence of membrane P-glycoprotein and without apparent changes in the cytoplasmic free $Ca^{2+}$concentration", Bioscience Reports vol. 10, No. 2, pp.231–237, (1990).

Twentyman, P.R., "Chemosensitisantion by verapamil nd cyclosporin A in mouse tumour cells expressing different levels of P-glycoprotein and CP22 (Sorcin)", Cancer vol. 62, pp.89–95 (1990).

Saeki, Tohru, "Human P-glycoprotein transports cyclosporin A and FK506", The Journal of Biological Chemistry vol. 268, No. 9, pp.6077–6080 (Mar. 25, 1993).

LIPOSOMAL CYCLOSPORIN FORMULATIONS AS AGENTS FOR IMMUNOSUPPRESSION AND MULTIPLE DRUG RESISTANT INDICATIONS

FIELD OF THE INVENTION

This invention relates to the fields of biochemistry and medicine, and in particular to a novel liposomal formulation and process. More specifically, it relates to a liposomal formulation containing the immunosuppressive agent cyclosporine and to its process of manufacture. This invention also relates to improved liposomal cyclosporine formulations having reduced toxicity and increased shelf life stability.

BACKGROUND OF THE INVENTION

The cyclosporines were discovered in 1970 by researchers in an attempt to identify new antimicrobial agents. Cyclosporine (also known as cyclosporin A), a potent immuno-suppressive agent, was isolated from two strains of imperfect fungi, *Cylindrocapon lucidum* Booth and *Tolypocladium inflatum* Gams.

Cyclosporins are hydrophobic, neutral, cyclical peptides which have essentially similar chemical and physical characteristics. Cyclosporine is a representative example, and consists of eleven amino acids with a total molecular weight of 1201. Cyclosporine is soluble in methanol, chloroform and ether and essentially insoluble in water. It is supplied for therapeutic purposes as either an intravenous preparation dissolved in a proprietary castor oil and alcohol, or an oral formulation dissolved in Labrophil and olive oil.

Cyclosporine is primarily used for treating allograft patients and has been used in experimental trials for autoimmune diseases. The use of this drug has greatly increased the survival rate of transplant patients since its advent in 1978.

Although cyclosporine is a very useful immunosuppressive agent, it can also be highly toxic when used for prolonged periods of time and/or at high doses, both of which are necessary to ensure graft acceptance. The most severe side effect associated with cyclosporine therapy is drug-induced nephrotoxicity. Vascular interstitial toxicity is the most common form of cyclosporine nephrotoxicity and can manifest itself as three different morphological lesions, occurring either alone or in combination. Although not all of these morphological changes associated with cyclosporine nephrotoxicity are unique to cyclosporine toxicity, if they are observed in combination with one another and there is also a corresponding high level of serum cyclosporine, the damage is probably a result of cyclosporine toxicity. Some individuals may show some of these adverse reactions at therapeutic doses (5 to 10 mg/kg/day) which produce trough levels of 200–500 ng/ml in whole blood and 20–60 ng/ml in serum. Renal toxicities can be monitored serologically by following the increase in creatinine levels. The increase in creatinine level is probably a direct result of arteriole constriction and blockage which would result in lower glomerular filtration rate and thus an increase in serum creatinine.

There are other adverse side reactions associated with cyclosporine treatment. These occur with varying frequencies depending on the type of transplant. They include symptoms, such as cardiovascular hypertension and cramps, skin hirsutism, gum hyperplasia, diarrhea, nausea, vomiting, hepatotoxicity, hematopoietic alterations including leukopenia and lymphoma, respiratory distress and sinusitis.

Other side effects associated with the intravenous delivery of cyclosporine are due to the intravenous carrier vehicle, Cremophor-El (CreL). CreL is a polyoxyethylated castor oil that is one of the best ionic surfactants used to dissolve lipophilic drugs. The most common of the adverse reactions associated with CreL administration has been anaphylaxis which results from a rapid release of histamine and causes increasing hypertension. It is also believed that part of the nephrotoxicity associated with cyclosporine treatment may be enhanced by CreL deposition and crystal formation within the kidney tubules. Other studies have also shown a decrease in both renal blood flow and creatinine clearance in animals treated with CreL. Riconic acid, a component of CreL, has been shown to cause vasoconstriction which could also be linked to hypertension and decreased glomerular blood flow.

Efforts have been made to eliminate the toxicity of cyclosporine by incorporating the drug into liposomes for purposes of administration, thus eliminating the toxic castor oil vehicle. Liposomes are microscopic delivery vesicles made, in part, from phospholipids which form closed, fluid filled spheres when mixed with water. Phospholipid molecules are polar, having a hydrophilic ionizable head, and a hydrophobic tail consisting of long fatty acid chains. Thus, when sufficient phospholipid molecules are present with water, the tails spontaneously associate to exclude water while the hydrophilic phosphate heads interact with water. The result is a bilayer membrane in which the fatty acid tails converge in the newly formed membrane's interior and the polar heads point in opposite directions toward an aqueous medium. The polar heads at one surface of the membrane point toward the aqueous interior of the liposome. At the opposite surface, the polar heads interact with the surrounding aqueous medium. As the liposomes form, water soluble molecules will be incorporated into the aqueous interior, and lipophilic molecules will tend to be incorporated into the lipid bilayer. Liposomes may be either multilamellar, like an onion with liquid separating many lipid bilayers, or unilamellar, with a single bilayer surrounding an entirely liquid center.

There are many types of liposome preparation techniques which may be employed and which produce various types of liposomes. These can be selected depending on the use, the chemical intended to be entrapped, and the type of lipids used to form the bilayer membrane.

Those parameters which must be considered in producing an optimal liposome preparation are similar to those of other controlled release mechanisms. They are as follows: (1) high percent of chemical entrapment; (2) increased chemical stability; (3) low chemical toxicity; (4) rapid method of production; and (5) reproducible size distribution.

The first method described to encapsulate chemicals in liposomes involved production of multilamellar vesicles (MLVs). The MLV process involves dissolving the lipid components in a suitable solvent, evaporation of the solvent to form a dry lipid film, and hydration of the lipid film with an aqueous medium. The multilamellar vesicles which form are structures having generally more than three concentric bilayers. Lipophilic drugs are incorporated into the MLVs by codissolution of the drugs in the solvent phase, while hydrophilic drugs are entrapped between the bilayers with the hydration buffer. By increasing the length of time of hydration and gentle shaking of the resuspending lipid film, one can achieve a higher proportion of the aqueous phase per mole of lipid, and thus enhance hydrophilic drug encapsulation. The increased entrapment of aqueous buffer can also be achieved by using charged lipids.

Liposomes can also be formed as unilamellar vesicles (UVs), which have diameters up to 2 μm, but generally less than 1 μm.

There are several techniques which are used to produce unilamellar liposomes. Large unilamellar vesicles (LUVs) can be formed using the reverse-phase evaporation method. This is done by removing the organic phase of a sonicated emulsion of phospholipid, buffer and excess organic solvent under pressure. This technique is especially useful for encapsulating large volumes of aqueous phase containing hydrophilic molecules, such as ferritin, 25S RNA or SV-40 DNA. Maximum encapsulation of the LUV aqueous phase (65%) can be obtained if the ionic strength of the aqueous buffer is low (0.01M NACl); encapsulation decreases to 20% as the ionic strength is increased to 0.5M NaCl. The size of the LUVs varies with the lipid and cholesterol content. Vesicles formed from cholesterol and phospholipid with a 1:1 mole ratio, form a heterogeneous size distribution of vesicles with a mean diameter, based upon entrapped volume, of 0.47 µm and a size range of 0.17–0.8 µm. Vesicles prepared from similar phospholipid mixtures lacking cholesterol have a mean size of 0.18 µm and a diameter range of 0.1–0.26 µm.

The solvent infusion evaporation method can produce both larger or smaller UVs, depending on variations in the technique. To form larger UVs, phospholipids are dissolved in diethylether and injected into a buffer maintained at 55°–65° C. containing the material to be entrapped or injected. The mixture is kept under vacuum at 30° C. When the solvent has evaporated, vesicles are formed. The range in diameter of these vesicles is from 0.25–1 µm. This procedure is well suited for entrapment for large molecules.

Smaller unilamellar vesicles can also be formed using a variety of techniques. By dissolving phospholipids in ethanol and injecting them into a buffer, the lipids will spontaneously rearrange into unilamellar vesicles. This provides a simple method to produce UVs which have internal volumes similar to that of those produced by sonication (0.2–0.5 L/mol/lipid). Sonication or extrusion (through filters) of MLVs also results in dispersions of UVs having diameters of up to 0.2 µm, which appear as clear or translucent suspensions.

Another common method for producing small UVs is the detergent removal technique. Phospholipids are solubilized in either ionic or non-ionic detergents such as cholates, Triton X, or n-alkylglucosides. The drug is then mixed with the solubilized lipid-detergent micelles. Detergent is then removed by one of several techniques: dialysis, gel filtration, affinity chromatography, centrifugation, or ultrafiltration. The size distribution and entrapment efficiencies of the UVs produced this way will vary depending on the details of the technique used. Also when proteins are entrapped, there is no certainty that once the detergent has been removed, the protein will renature into its native bioactive conformation.

The therapeutic use of liposomes includes the delivery of drugs which are normally very toxic in the free form. In the liposomal form the toxic drug may be directed away from the sensitive tissue and targeted to selected areas. Liposomes can also be used therapeutically to release drugs slowly, over a prolonged period of time, reducing the frequency of administration. In addition, liposomes can provide a method for forming an aqueous dispersion of hydrophobic drugs for intravenous delivery.

When liposomes are used to target encapsulated drugs to selected host tissues, and away from sensitive tissues, several techniques can be employed. These procedures involve manipulating the size of the liposomes, their net surface charge as well as the route of administration. More specific manipulations have included labeling the liposomes with receptors or antibodies for particular sites in the body.

The route of delivery of liposomes can also affect their distribution in the body. Passive delivery of liposomes involves the use of various routes of administration e.g., intravenous, subcutaneous and topical. Each route produces differences in localization of the liposomes. Two common methods used to actively direct the liposomes to selected target areas are binding either antibodies or specific receptor ligands to the surface of the liposomes. Antibodies are known to have a high specificity for their corresponding antigen and have been shown to be capable of being bound to the surface of liposomes, thus increasing the target specificity of the liposome encapsulated drug.

Since the chemical composition of many drugs precludes their intravenous administration, liposomes can be very useful in adapting these drugs for intravenous delivery. Many hydrophobic drugs, including cyclosporine, fall into this category because they cannot be easily dissolved in a water-based medium and must be dissolved in alcohols or surfactants which have been shown to cause toxic reactions in vivo. Liposomes, composed of predominantly lipids, with or without cholesterol, are nontoxic. Furthermore, since liposomes are made of amphipathic molecules, they can entrap hydrophilic drugs in their interior space and hydrophobic molecules in their lipid bilayer.

In prior applications, it was shown that liposome encapsulated cyclosporin can be formulated having high entrapment, characteristics along with good stability; U.S. application Ser. No. 07/687,812) now abandoned and U.S. application Ser. No. 08/417,487), both incorporated herein by reference. These formulations were also shown to be efficacious in suppressing immune response in the cells of mammals and reducing multiple drug resistance of cancer cells. Other formulations have been shown to be stable in mammalian blood (U.S. patent application Ser. No. 08/475, 294, entitled "Blood Stable Liposomal Cyclosporin").

In a drive to develop a formula that is both safe and effective, such as required by the Food and Drug Administration, it is desirable to provide formulations that have long shelf life stability. Unilamellar liposomes in many cases tend to aggregate and become larger over time. This is one parameter that indicates that the liposomes are not stable. Of course other parameters indicate unstable liposomes such as drug loss over time (leakage).

Thus, for a variety of reasons, having to do primarily with the inability of those of ordinary skill to entrap sufficient cyclosporins in a stable liposomal carrier, a therapeutically effective cyclosporin intercalated liposome product has not been commercially available. It has thus been a desideratum to develop a liposomal cyclosporin containing a formulation which enables a high proportion of the active agent to be incorporated therein, and which is sufficiently stable on the shelf. This invention provides such a product.

Thus, an object of the present invention is to provide an improved liposome encapsulated cyclosporin formulation that has superior shelf life stability and improved toxicity.

SUMMARY OF THE INVENTION

An improved cyclosporin liposomal formulation is provided. The formulation is a therapeutic formulation and it includes liposomes comprised of phosphatidylcholine, cholesterol, phosphatidylglycerol and cyclosporin having a mole ratio of about 21:0.5:3:1 to 21:1.5:3:1 and 24:0.5:3:1 to 24:1.5:3:1 wherein the liposomes comprise unilamellar vesicles having a size less than 100 nm. The liposomes are efficacious as immunosuppression agents and in the treatment of drug resistant cancers.

More specifically, a stable liposomal cyclosporin therapeutic formulation is prepared by a process which comprises the steps of:

(a) dissolving (i) a phosphatidylcholine, (ii) a cholesterol (iii) a compound selected from the group consisting of a phosphatidylglycerol, phosphatidic acid, or mixtures thereof and (iv) a cyclosporin in an organic solvent to form a solution wherein the molar ratio of (i) to (ii) to (iii) to (iv) ranges from about 21:0.5:3:1 to 21:1.5:3:1 and 24:0.5:3:1 to 24:1.5:3:1, (b) drying the organic solution thus formed to form a solid phase, e.g., a film or powder, (c) hydrating the solid phase with an aqueous solution having a pH from about 4.5 to about 9.5 to form the stable liposomal cyclosporin therapeutic formulation having a mean particle size of less than 100 nm.

Preferred formulations of the present invention are formulated with and are suspended in an aqueous solution having a pH ranging from about 5.5 to about 8.5.

The invention provides a novel process and a cyclosporin intercalated liposomal formulation which is stable on storage, contains a therapeutically effective amount of active ingredient, and provides a liposomal cyclosporin formulation having reduced toxicity. The process of the invention provides a commercially feasible process for the production of a liposomal cyclosporin. The formulations are particularly useful in suppressing an immune response in cells and mammals, in reducing multiple drug resistance of cancer cells and inhibiting the growth of cancer cells.

DETAILED DESCRIPTION OF THE INVENTION

As used herein, the term liposome refers to unilamellar vesicles or multilamellar vesicles such as described in U.S. Pat. Nos. 4,753,788 and 4,935,171, the contents of which are incorporated herein by reference. The term encapsulation as used herein refers to the incorporation of a cyclosporin into the liposome membrane.

Generally, the process of preparing the formulation embodied in the present invention is initiated with the preparation of a solution from which the liposomes are formed. This is done by weighing out a quantity of phosphatidylcholine, cholesterol, dimyristoylphosphatidylglycerol and cyclosporine, preferably cyclosporine, and dissolving them into an organic solvent, preferably chloroform and methanol in a 1:1 mixture. The quantity of phosphatidylcholine, cholesterol, phosphatidylglycerol, and cyclosporin is weighed out at in a mole ratio within the range of about 21:0.5:3:1 to about 21:1.5:3:1 and from about 24:0.5:3:1 to about 24:1.5:3:1. The preferred formulation is about 24:1:3:1. The solution is dried until a lipid film or powder is made. The lipid film or powder is added to a phosphate or succinate buffer. The buffer may contain a disaccharide such as sucrose. The pH of the buffers is within the range of about 4.5 to 9.5. This solution forms a hydrated liposome dispersion. The lipid film or powder is hydrated between room temperature and 65° C., preferably at 60° C. The unilamellar vesicles are formed by applying a shearing force to the dispersion, e.g., by sonication or by the use of a homogenizing apparatus such as a Gaulin homogenizer or a French press. Shearing force can also be applied using either injection, freezing and thawing, dialyzing away a detergent solution from lipids, or other known methods used to prepare liposomes. The preferable temperature during sonication is about 65° C. The size of the liposomes can be controlled using a variety of known techniques including the duration of shearing force. Preferably, the modified Gaulin homogenizing apparatus described in U.S. Pat. No. 4,753,788 is employed to form unilamellar vesicles having diameters of less than 100 nm at a pressure of 4,000 to 13,000 psi and a temperature of about the aggregate transition temperature of the lipids.

Distearoylphosphatidylcholine (DSPC) and dimyristoylphosphatidylglycerol (DMPG) are the preferred lipids for use in the invention. The preferred size of liposomes is below 45 nm. The preferred percent entrapped cyclosporine is about 85% or greater.

The liposomes of the invention as practiced herein, show improved shelf life stability, i.e., no significant (visual) aggregation for at least 9 weeks at 4° C.

The invention also provides a method for suppressing an immune response in a mammal by the delivery of a therapeutic or effective amount of a liposomal cyclosporin formulation. The formulations are useful for the treatment of autoimmune diseases and in the treatment of allograft patients. In another aspect of the present invention, a method is provided for reducing multiple drug resistance of a cancer cell by delivering a therapeutic or effective amount of a cyclosporin, preferably cyclosporine, liposomal formulation to a mammal. To effectuate the reduction in the multiple drug resistance of a cancer cell the cyclosporin is used in a treatment combination with an antineoplastic or anticancer agent. Although the cyclosporin is used in combination with the antineoplastic or anticancer agent, it is not necessary for them to be delivered simultaneously. In yet another aspect of the invention, a method of inhibiting the growth of cancer cells, both drug resistant and drug sensitive, is provided by delivering a therapeutic or effective amount of free cyclosporin or liposomal cyclosporin to cancer cells, preferably in a mammal. Since dosage regimens for cyclosporins are well known to medical practitioners, the amount of the liposomal cyclosporin formulations which is effective or therapeutic for the treatment of the above mentioned diseases or conditions in mammals and particularly humans will be apparent to those skilled in the art.

EXAMPLE 1

A series of liposome formulations containing cyclosporine were prepared. DSPC, cholesterol, DMPG and cyclosporine (21:1.5:3:1, 21:1:3:1, 24:1.5:3:1 and 24:1:3:1 respectively) were dissolved in a mixture of chloroform and methanol (1:1 by volume) and the solution formed was dried under nitrogen until a dried film was obtained. The lipid film was placed in a desiccator under vacuum for at least 8 hours to remove the residual organic solvent. The dried film was hydrated at 65° C. for ten minutes in 10 mM sodium succinate in 9% sucrose pH=6.75. Unilamellar vesicles were formed by sonicating the solution for 15 minutes at 65° C. until a translucent solution was obtained. The solution was incubated at 65° C. for 10 minutes. The solution was centrifuged at 3600 rpm for 10 minutes and the supernatant was collected. The concentration of lipids and cyclosporine was determined by HPLC. The size of the vesicles was determined by optical particle sizing. The results are listed in Table 1.

TABLE 1

ENCAPSULATION WITH VARYING MOLAR RATIOS OF CYCLOSPORINE

| Mole Ratio (DSPC:Chol:DMPG: Cyclosporine) | % Cyclosporine Entrapped | Size by Mean Diameter (nm) |
| --- | --- | --- |
| 21:1.5:3:1 | >90 | 38.0 |
| 21:1:3:1 | >90 | 37.3 |
| 24:1.5:3:1 | >90 | 46.7 |
| 24:1:3:1 | >90 | 34.1 |

All samples of Table 1 show no visible signs of aggregation after nine weeks at 4° C.

EXAMPLE 2

Multiple Drug Resistance (MDR) Testing in P388/ADR Cells

In order to test the effect of doxorubicin with cholesterol-containing formulations of liposomal cyclosporin A, the following experiment was done. Fifty microliters of the appropriate Doxorubicin (Dox) concentration was added to the wells of a flat bottom 96-well culture plate. In addition, 50 µl of liposomal formulations prepared as in Example 1, or free Cyclosporin A (CsA Crel), were added to the wells. All experiments were done in triplicate. The P388/ADR cells were grown 24 hrs in complete RPMI-1640 and then centrifuged at 1000 rpm for 10 min. The cell pellet was adjusted to $1\times10^5$ cells/ml in RPMI-1640+20% FCS+2% FCS and 1% pen-strep, and the plates were incubated for 24 hrs at 37° C. (Positive control wells only contained cells and media, and negative control wells contained cells, media, and 20 µl of 1.5M Tris buffer).

After 20 hours of incubation, the plates were pulsed with 0.5 µCi of $^3$H-Thymidine per well and incubated for an additional 4 hours. Next, the cells were harvested using a Tomtec harvester and counted on a Betaplate scintillation counter. Linear regression analysis was used to determine the IC-50's of the various cyclosporin A treatments and the doxorubicin IC-50 values were graphed as a function of CsA concentration.

The results of the tests are displayed in Table 2.

TABLE 2

Comparison of Cyclosporine-containing Formulations

| Formulation | Toxicity at 1800 ng/ml | Dox IC-50 at 1800 ng/ml of CsA |
| --- | --- | --- |
| Free drug | 15% | 446 |
| (19:0:3:1) | 30% | 429 |
| 21:1.5:3:1 | 12% | 308 |
| 21:1:3:1 | 10% | 421 |
| 24:1.5:3:1 | 0% | 477 |
| 24:1:3:1 | 0% | 367 |

The cholesterol-containing liposomal formulations tested demonstrated a reversal of the MDR in P388/ADR cells. However, some of the formulations were more efficacious than others.

The formulations demonstrate low toxicity and good reversal of MDR.

EXAMPLE 3

Immunosuppressive Efficacy of 24:1:3:1 Formula

A DSPC:Chol:DMPG:CSA formulation (24:1:3:1) was prepared as described in Example 1. The following experiment was performed to compare the ability of various liposomal cyclosporin formulations, given in vivo, to suppress the splenic lymphocyte response to in vitro stimulation by concanavalin A (ConA) as compared to cyclosporine in complex L (CSA CreL, sandimmune, SA). Mice were sacrificed and their spleens removed and placed in RPMI-1640 medium with 2% pen-strep (Gibco). A single cell suspension was made from each spleen by passing it through a 70 µm nylon mesh sieve (Falcon). The sieve was rinsed with RPMI+2% pen-strep to obtain a 10 ml volume of cell suspension. The splenic cell suspension was centrifuged at 1000 rpm for 8 min. and the supernatant was removed. The red blood cells were lysed with 1 ml lysing buffer (Cardinal Assoc. lot #09406 exp. January 1997) for 1 min., then centrifuged at 10000 rpm for 8 min. and the supernatant was removed. The cell pellet was resuspended in RPMI+5% FCS+1 pen-strep, and cell viability determined by trypan blue staining. The cells were then adjusted to a cell concentration of to $5\times10^6$ cells/ml. Then the splenic lymphocytes were plated into the wells of a 96-well round bottom plate at 0.1 ml/well ($5\times10^5$ cells/well).

Concanavalin A was diluted in PBS, aliquoted, and stored in a frozen state at −70° C. prior to use. A 1 ml aliquot was thawed and diluted 1:4 in RPMI +5% FCS+1% pen-strep. The stock solution was diluted in RPMI+5% FCS+1% pen strep to obtain working solutions of 3 µCi $^3$H-Thymidine (ICN Radiochemicals) per well on day 2. The cells were harvested onto glassfibre filtermats on day 3 using a Tomtec cell harvester. The filtermats were dried overnight, placed in sample bags with 10 ml Betascint cocktail, and the incorporated $^3$H-Thymidine counted on a Betaplate scintillation counter (Wallac). The counts per minute (cpm) for triplicate wells were averaged, and the mouse treatment groups were averaged. The Δ cpm was calculated by subtracting the average cpm at ConA=0 µg/ml from the average cpm at each ConA level. From these values, the percentage inhibition relative to the control was calculated by the following formula: % Inhibition=(Δ cpm saline−Δ cpm experimental )/Δ cpm saline*100

A non-radioactive cell proliferation ELISA assay, the BrdU assay, was also performed on these samples. The plates were incubated as described above. On day 2, the wells were labelled with 20 µl/well of 100 µM BrdU labelling solution (5-bromo-2'deoxyuridine; Boehringer-Mannheim) for 19 hours. The culture medium was removed by centrifuging the plates (300 g, 10 min) and pipetting off 175 µl of medium. The plates were dried for 2.5 hr at 65° C. FixDent solution was added (200 µl/well) and incubated for 30 min at room temp (RT). The FixDent solution was removed and 100 µl/well of anti-BrdU-POD solution was added. The plates were incubated for 90 min at RT, then washed three times with washing buffer. The substrate solution was added (100 µl/well) for 7 min at RT. The substrate reaction was stopped by adding 25 µl/well of 1M $H_2SO_4$. The absorbance was immediately measured at 450 nm using a microplate reader (Titertek). The absorbance values for triplicate wells were averaged, and the mouse treatment groups were averaged. The A absorbance (A) was calculated by subtracting the average absorbance at ConA=0 µg/ml from the average absorbance at each ConA level. From these values, the percentage Inhibition relative to the control was calculated by the following formula:

% Inhibition=(Δ saline−Δ A experimental)/Δ A saline*100

The following results were obtained. In the $^3$H thymidine assay at 1.5 µg/ml ConA, 2.0 µg/ml ConA and 3.5 µg/ml the CSA-CreL showed approximately 5%, 12.5% and 2% inhibition, respectively. The liposomal formulation at the same ConA concentrations (24:1:3:1) showed 13%, 10% and 3% inhibition respectively.

In the BrdU assay CSA-CreL at 1.5 µg/ml ConA and 2.4 µg/ml ConA showed approximately 30%, 30%, and 70% inhibition respectively. The liposomal formulation (24:1:3:1) at the same ConA concentrations showed approximately 52%, 52% and 75% inhibition respectively.

Although this specification has disclosed and illustration with reference to particular applications, the principles involved are susceptible to numerous other applications which will be apparent to those skilled in the art. The invention is, therefore, to be limited only as indicated by the scope of the appended claims.

What is claimed is:

1. Liposomes having a size less than 100 nm comprising a phosphatidylcholine, cholesterol, dimyristoylphosphatidylglycerol and cyclosporin in a mole ratio from about 21:0.5:3:1 to about 21:1.5:3:1.

2. The liposomes of claim 1 wherein the phosphatidylcholine is distearoylphosphatidylcholine.

3. Liposomes having a size less than 100 nm comprising a phosphatidylcholine, cholesterol, dimyristoylphosphatidylglycerol and cyclosporin in a mole ratio of about 24:0.5:3:1 to about 24:1.5:3:1.

4. The liposomes of claim 3 wherein the phosphatidylcholine is distearoylphosphatidylcholine.

5. The liposomes of claim 3 wherein the mole ratio of phosphatidylcholine, cholesterol, dimyristoylphosphatidylglycerol and cyclosporin is about 24:1:3:1.

6. The liposomes of claim 4 wherein the mole ratio of distearoylphosphatidylcholine, cholesterol, dimyristoylphosphatidylglycerol and cyclosporin is about 24:1:3:1.

7. The liposomes of claim 1 wherein said liposomes are free of substantial aggregation for at least nine weeks at 4° C.

* * * * *